United States Patent [19]

Yang

[11] 4,446,153

[45] May 1, 1984

[54] SKIN SANITIZING COMPOSITION AND METHOD OF USING

[75] Inventor: Kim W. Yang, St. Louis, Mo.

[73] Assignee: Ralston Purina Company, St. Louis, Mo.

[21] Appl. No.: 430,089

[22] Filed: Sep. 30, 1982

[51] Int. Cl.$^3$ ............................................. A61K 31/045
[52] U.S. Cl. ...................................................... 424/343
[58] Field of Search ........................................... 424/343

[56] References Cited

U.S. PATENT DOCUMENTS

| | | | |
|---|---|---|---|
| 3,663,716 | 5/1972 | Stolar | 424/343 |
| 4,006,218 | 2/1977 | Sipos | 424/343 |
| 4,376,787 | 3/1983 | Lentsch et al. | 424/315 |

OTHER PUBLICATIONS

Nakamura–Chem. Abst. vol. 69 (1968) p. 41952e.

McCulloch et al–Chem. Abst. vol. 65 (1966) p. 10997c.

*Primary Examiner*—Sam Rosen
*Attorney, Agent, or Firm*—Virgil B. Hill

[57] ABSTRACT

A skin sanitizing composition is disclosed which is particularly suited as a teat dip or udder wash for dairy cows which comprises at least one phenyl alkanol such as benzyl or phenethyl alcohol as the microbiocidal or sanitizing ingredient in an amount effective to substantially reduce the bacteria population on a skin surface when the composition is applied thereto. An emulsifying amount of a surfactant is included to provide an aqueous dispersion of the phenyl alkanol ingredient, which enhances the germicidal activity of the microbiocidal or sanitizing ingredient. The composition may include an emollient if desired and has a typical pH of between about 4 and 7.

22 Claims, No Drawings

SKIN SANITIZING COMPOSITION AND METHOD OF USING

BACKGROUND OF THE INVENTION

The present invention relates to a skin sanitizing composition, particularly a teat dip or udder wash for the treatment of dairy cows.

Dairy cows are commonly effected by a disease known as mastitis which occurs by organisms entering the mammary glands through the teat canal. Mastitis renders the cows unsuitable for milking and a significant level of cows effected with mastitis in a herd can result in a significant economic loss to the farmer.

It is common practice in the dairy industry to apply a composition to the teats of the cow, usually immediately following milking, in order to prevent bacteria growth on the teat surface and penetration of the teat canal. While the present invention relates broadly to skin sanitizing compositions for any type of mammal, nevertheless, it is for use as a teat dip or udder wash that the composition of the present invention has particular application and for which purpose the following description is made. Since the teats of diary cows represent a very sensitive skin area, the particular teat dip or udder wash used must not only significantly reduce or kill the bacteria population on the skin surface but must further prevent significant bacteria growth for an extended period of time. It is even more important that the particular dip also be non-irritating to such a sensitive skin area as the teat surface.

A variety of products have been proposed over the years as teat dips for dairy cows among the most widely used of which are compositions containing iodine as the active microbiocidal ingredient. While iodine is an extremely efficient microbiocide, it can be irritating to the skin surface, particularly such a sensitive surface as a teat. This limits somewhat its usefulness since even if bacterial contamination of the skin surface is eliminated the possible irritation caused by the iodine effectively limits milking of the animals as well. Also, more recently concern has been expressed over the use of iodine as a teat dip because of possible contamination of the milk. Therefore, a need has existed for a non-irritating teat dip composition which avoids the use of iodine as the microbiocidal ingredient.

U.S. Pat. No. 4,258,056 for example, describes a teat dip composition comprising a combination of an anionic surfactant and an aminocarboxylic type chelating agent. U.S. Pat. No. 3,558,788 describes a teat dip biocide containing a nitroalkanol such as 2-bromo-2-nitropropane. U.S. Pat. No. 4,199,564 also describes a teat dip without the use of iodine which includes a water soluble lower alkanol microbiocide in an amount of 15 to 70% by weight together with a film forming polymer and an emollient.

In spite of the disclosure of iodine free teat dip products of the type generally disclosed above, a need has still existed for a skin sanitizing composition such as a teat dip or udder wash which contains a relatively low percentage of microbiocide or active ingredient to avoid a significant degree of skin irritation together with the ability to effectively or substantially reduce the bacteria population on a teat surface and maintain this low population for an extended period of time. These advantages have been achieved in the present invention wherein a skin sanitizing composition is obtained having a low degree of skin irritation but is extremely effective in reducing bacterial contamination of the skin surface.

It is therefore an object of the present invention to provide a skin sanitizing composition which is relatively non-irritating yet substantially reduces the bacteria population when applied to a surface.

It is a further object of the present invention to provide a skin sanitizing composition which is particularly useful as an udder wash or teat dip for application to dairy cows.

SUMMARY OF THE INVENTION

The present invention relates to a skin sanitizing composition particularly useful as a teat dip or udder wash for dairy cows comprising at least one phenyl alkanol as the active microbiocidal or sanitizing ingredient present in an amount effective to substantially reduce the bacteria population on the skin surface when said composition is applied to a skin surface, said composition including an emulsifying amount of a surfactant to provide an aqueous dispersion of the microbiocidal or sanitizing ingredient, said skin sanitizing composition having a pH of between about 4 and 7.

This skin sanitizing composition is highly effective as a teat dip or udder wash and selectively reduces as well as inhibits the growth of both gram negative and gram positive microorganisms. While a phenyl alkanol has been previously recognized as a relatively good preservative for various products, it is considered to be a relatively poor microbiocide or sanitizer because of the length of time required to kill microorganisms even at a relatively high concentration. Therefore, in the present invention, is was unexpectedly determined that if at least one phenyl alkanol is included in the teat dip together with a surfactant that the germicidal or sanitizing effect of the phenyl alkanol is enhanced, thereby making it eminently suitable as a relatively non-irritating microbiocidal component of an udder wash or teat dip for dairy cattle.

DESCRIPTION OF THE PREFERRED EMBODIMENTS

As broadly stated, the skin sanitizing composition of the present invention comprises as the primary ingredient a microbiocide or germicide comprising at least one phenyl alkanol. The phenyl alkanol is added to the skin sanitizing composition of the present invention in an amount effective to substantially reduce the bacteria population on a skin surface when the composition is applied thereto. The phenyl alkanol added as the microbiocidal or sanitizing ingredient of the composition of the present invention is of the following general formula:

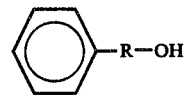

wherein R is selected from the group consisting of $CH_2$, $C_2H_4$, $C_3H_6$, $C_4H_8$ and

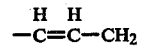

derivatives. Therefore, the preferred phenylalkanols for use in the present invention are phenylmethanol (benzyl alcohol), phenylethanol, phenylpropanol, phenylbutanol, and phenyl allyl alcohol (cinnamyl alcohol). At least one of these phenyl alkanols is included in the skin sanitizing composition of the present invention, and it is preferred for purposes of the present invention that more than one phenyl alkanol be included in the composition to provide the maximum degree of effectiveness against most types of microorganisms and thereby effectively sanitize the skin surface. It is particularly preferred that a combination of two phenyl alkanols, specifically phenyl methanol (benzyl alcohol) and phenyl ethanol be used in combination as the microbiocidal ingredient of the composition of the present invention. This specific combination of phenyl alkanols effectively reduces or destroys most gram positive as well as gram negative microorganisms and together provides the required degree of sanitation on the skin surface.

At least one or more of the phenyl alkanols are present in the skin sanitizing composition or teat dip of the present invention in an amount effective to substantially reduce the bacteria population on a skin surface that the composition is applied to. Typical amounts of the phenyl alkanol ingredient are between about 0.8–6% by weight of the skin sanitizing composition, and preferably between about 2 to 4% by weight of the composition.

Another essential ingredient of the skin sanitizing composition or teat dip of the present invention is a surfactant since typically, the above ingredients such as the phenyl alkanols are not soluble in water thereby requiring the addition of a surfactant to effectively emulsify the ingredients for use in an aqueous dispersion. Furthermore, the use of a surfactant in combination with the phenyl alkanol active ingredient unexpectedly enhances the germicidal activity of the phenyl alkanol ingredient in an aqueous dispersion. The specific type of surfactant which may be added to the skin sanitizing composition of the present invention is not critical to its practice and may be selected from a wide variety of materials including anionic, cationic, and non-ionic surfactants provided that the surfactant or surface active agent does not substantially deactivate the microbiocidal ingredient. Typical and suitable emulsifiers are the anionic surfactants which include the sulfonated detergents which comprises sulfonated fatty acids or sulfonated aliphatic hydrocarbon residues. A wide variety of sulfonated detergent surfactants are available for use in applications such as that described in the present invention. Specific suitable anionic surfactants include materials such as sodium lauryl sulfate, sodium lauryl sarcosinate and sodium dodecyl benzenesulfonate.

Cationic surfactants are equally suitable for use in the skin sanitizing composition of the present invention and these include materials such as dimethylammonium chloride and cetyl trimethylammonium chloride both of which are commonly used cationic surfactants or detergents. Alternatively, various non-ionic surfactants such as n-alkyl ($C_{12}$–$C_{16}$) dimethylammonium oxide may also be employed in preparation of the skin sanitizing composition of the present invention. Any of the above surfactants are combined with the phenyl alkanol microbiocidal ingredient of the present invention in an emulsifying amount preferably in an amount sufficient to provide dispersion of the phenyl alkanol microbiocidal ingredients in an aqueous solution.

Preferred surfactants for use in the present invention include the anionic surfactant such as sodium lauryl sulfate and sodium dodecyl benzene sulfonate since these surfactants will emulsify relatively large amounts of water insoluble materials and provide relatively stable suspensions even at extreme temperatures of storage. Typical amounts of surfactant which may be used in preparing the skin sanitizing composition of the present invention are between about 0.5 to 6% by weight of the composition.

A preferred and well known ingredient which may be added to the skin sanitizing composition or teat dip of the present invention is an emollient since the emollient provides a softening effect on the skin surface when applied thereto thereby promoting the effectiveness of the sanitizing composition of the present invention. Typical emollients which may be used in the composition of the present invention include the polyhydric alcohols such as glycerol propylene glycol or sorbitol. This is not a critical ingredient for purposes of the present invention and may be omitted if desired since it does not enter into the sanitizing effect of the composition, nevertheless, it is preferred for purposes of skin softening and reduces the degree of irritation of the microbiocidal ingredients on the skin surface. Therefore, typical amounts of the emollient which may be added to the teat dip of the present invention are between about 0 to 10% by weight of the composition.

Another optical ingredient of the skin sanitizing composition or teat dip of the present invention is the use of a thickening material such as water soluble vinyl compounds, gums and the like for the purposes of making a thickened or lotion type of suspension which can be easily applied to a skin surface to provide adherence of the active ingredients on the skin surface because of the thick nature of the aqueous dispersion.

The skin sanitizing composition of the present invention is particularly effective when the ph is between about 4 to 7 and preferably between about 4 to 5. The addition of various materials such as citric acid or sodium hydroxide or combinations thereof may be easily added to the aqueous solution to provide the required pH level for purposes of effective control of bacteria populations on the skin surface without resultant irritation thereof.

Various other ingredients not critical to the function of the skin sanitizing composition of the present invention may be used if desired such as mold inhibitors and the like to provide shelf stability or similar functions. A suitable coloring agent may also be added if desired so as user of the composition may readily determine when a skin surface has been treated with the composition.

The skin sanitizing composition or teat dip of the present invention is particularly suitable for use in the treatment of the teats of dairy cattle to prevent bacterial contamination and resultant high incidence of mastitis. The active germicidal ingredients of the composition of the present invention effectively reduce bacteria populations without a high degree of skin irritation and avoid the need for highly toxic bactericides such as iodine and the like. It has been determined that the composition of the present invention is relatively effective in controlling bacterial levels on a teat surface without significant degree of irritation upon prolonged and repeated application of the composition.

The following examples represent specific but non-limiting embodiments of the present invention.

EXAMPLE 1

A skin sanitizing composition was prepared from the following ingredients:

| Ingredient | % by Weight |
| --- | --- |
| Water | 93.07 |
| Benzyl Alcohol | 4.00 |
| Dodecyl benzene Sulfonic Acid | 2.00 |
| Citric Acid | 0.50 |
| Sodium Hydroxide | 0.43 |
| Total | 100.00 |

The water, benzyl alcohol, and dodecyl benzene sulfonic acid were mixed for 1 minute, followed by the addition of the noted amounts of citric acid and sodium hydroxide. Mixing was performed for an additional 5 minutes and the composition had a pH of 4.0–4.5.

EXAMPLE 2

A skin sanitizing composition was prepared as described in Example 1 except that 4.0% by weight of phenyl ethyl alcohol was substituted for the Benzyl Alcohol.

EXAMPLE 3

A skin sanitizing composition was prepared as described in Example 1 except that 4.0% by weight of phenyl propyl alcohol was substituted for the Benzyl Alcohol.

EXAMPLE 4

A skin sanitizing composition was prepared as described in Example 1 except that 4.0% by weight of phenyl butyl alcohol was substituted for the Benzyl Alcohol.

EXAMPLE 5

A skin sanitizing composition was prepared as described in Example 1 except that 4.0% by weight of phenyl allyl alcohol (cinnamyl) was substituted for the benzyl alcohol.

EXAMPLE 6

The skin sanitizing composition formulated as described in Examples 1–5 were evaluated for effectiveness in the Association of Official Analytical Chemists Germicide (AOAC) and Detergent Sanitizer Test as described in *Official Methods of Analysis of the AOAC*, Thirteenth Edition (1980): 4.023–4.032. These results are set forth in Table 1.

TABLE 1

| | | Microbes Used | |
| --- | --- | --- | --- |
| Example | Microbiocide | *Staphylococcus aureus* ATCC NO 6538 | *Escherichia coli* ATCC 11229 |
| 1 | Benzyl Alcohol | Passes | Passes |
| 2 | Phenethyl Alcohol | Passes | Passes |
| 3 | Phenpropyl Alcohol | Passes | Passes |
| 4 | Phenbutyl Alcohol | Passes | Not Performed |
| 5 | Cinnamyl Alcohol | Passes | Passes |

It is apparent from the above data that the skin sanitizing compositions prepared according to Examples 1–5 are effective as a germicide or sanitizing composition as measured by the above test.

EXAMPLE 7

A skin sanitizing composition was prepared from the following ingredients:

| Ingredient | % by Weight |
| --- | --- |
| Water | 95.07–96.07 |
| Phenyl Alkanol | 1.00–2.00 |
| Dodecylbenzene Sulfonic Acid | 2.00 |
| Citric Acid | 0.50 |
| Sodium Hydroxide | 0.43 |
| | 100.00% |

The ingredients were mixed as described in Example 1 to result in a composition having a pH of 4.0–4.5. Various phenyl alkanols or mixtures thereof, at several different levels were employed in the above general formula, then evaluated for effectiveness in the Association of Official Analytical Chemists (AOAC) Germicide and Detergent Sanitizer Test as described in *Official Methods of Analysis of the AOAC*, Thirteenth Edition (1980) 4.023–4.032. The listing of the various alkanols and amounts tried are listed in Table 2 together with the results of the testing.

TABLE 2

| | | | Microbes Used | |
| --- | --- | --- | --- | --- |
| Test | Phenyl Alkanol (Microbiocide) | % By Weight | *Staphylococcus aureus* ATCC NO 6538 | *Escherichia coli* ATCC 11229 |
| 1 | Benzyl Alcohol | 1.00 | Passes | Fails |
| 2 | Phenethyl Alcohol | 1.00 | Passes | Fails |
| 3 | Benzyl Alcohol<br>Phenethyl Alcohol | 1.00<br>1.00 | Passes | Passes |
| 4 | Benzyl Alcohol | 2.00 | Passes | Fails |
| 5 | Phenethyl Alcohol | 2.00 | Passes | Passes |

It may be seen that while specific phenyl alkanols perform satisfactorily in the above test against a specific type of microorganism, it is preferred that a mixture of more than one phenyl alkanol be employed for purposes of a wider range of germicidal effect against both gram positive and gram negative microorganisms.

EXAMPLE 8

A skin sanitizing composition was prepared from the following ingredients:

| Ingredient | % by Weight |
| --- | --- |
| Water | 95.07 |
| Benzyl Alcohol | 1.00 |
| Phenethyl Alcohol | 1.00 |
| Surfactant | 2.00 |
| Citric Acid | 0.50 |
| Sodium Hydroxide | 0.43 |
| | 100.00% |

The above ingredients were mixed as generally described in Example 1 and the composition had a pH of 4.0–4.5. Various surfactants or emulsifiers were employed at the noted level of addition, then the compositions with the various surfactants were evaluated for effectiveness in the Association of Official Analytical Chemists (AOAC) Germicide and Detergent Sanitizer Test as described in *Official Methods of Analysis of The AOAC*, Thirteenth Edition (1980) 4.023–4.032. The listing of the various surfactants employed are set forth in Table 3 together with the results of the testing.

TABLE 3

| Surfactant | Types of Surfactant | Microbes Used | |
|---|---|---|---|
| | | *Staphylococcus aureus* ATCC No. 6538 | *Escherichia coli* ATCC 11229 |
| Sodium Dodecyl benzene Sulfonate | Anionic | Passes | Passes |
| Sodium Lauryl Sulfate | Anionic | Passes | Passes |
| Sodium Lauroyl Sarcosinate | Anionic | Passes | Passes |
| n-Alkyl ($C_{12}$–$C_{16}$) Dimethyl Ammonium Oxide | Nonionic | Passes | Passes |
| n-Alkyl ($C_{12}$–$C_{16}$) Dimethyl Ammonium Chloride | Cationic | Passes | Passes |
| Cetyl Trimethyl Ammonium Chloride | Cationic | Passes | Passes |

The above data illustrates that a variety of surfactants satisfactorily perform in the skin sanitizing composition of the present invention as measured by the above procedure.

EXAMPLE 9

A teat dip was prepared from the following ingredients:

| Ingredient | % by Weight |
|---|---|
| Water | 84.091 |
| Polyhydric Alcohol (Emollient) | 10.000 |
| Dodecyl Benzene Sulfonic Acid (Surfactant) | 2.000 |
| Benzyl Alcohol | 1.000 |
| Phenethyl Alcohol | 1.000 |
| Citric Acid (50% solution) | 0.740 |
| Sodium Hydroxide | 0.409 |
| Fungistat | 0.750 |
| FD&C Green #3 | 0.010 |
| | 100.00% |

This was produced in the general manner described in Example 1 and had a pH between 4.0–4.5.

EXAMPLE 10

The teat dip described in Example 9 was evaluated to determine the effectiveness of the teat dip in reducing the number of mastitis pathogens on the skin of excised cow teats. The experimental design for measuring the effectiveness of the dip on excised teat dips is set forth in Protocol A entitled "Proposed Protocol for Screening Teat Dips for Effectiveness by Reducing Bacteria Populations on Excised Cow Teats", Nov. 1, 1977 published by the National Mastitis Council, 910 Seventeenth Street N.W., Washington, D.C. 20006.

The teat dip of Example 9 was evaluated in the above procedure as compared to a positive control which consisting of a teat dip employing 1% iodine as the germicidal or sanitizing component. This iodine containing dip is specifically described as a surfactant Iodine Complex or Iodophor Type Teat Dip. A negative control was employed in which no sanitizer or dip was applied to an excised teat. The above protocol generally comprises applying one or more known mastitis pathogens of known concentration suspended in milk to excised teats. No teat dip is applied to some of the excised teats to which the pathogens have been applied and this represents the negative control. The other excised teats are treated with the germicidal solution to be tested. A comparison is made between the numbers of colony forming units of the pathogens recovered from the control and dipped teats by a standardized rinsing and culturing procedure. The geometric mean count for teats of the control and treated group are reported. It is normally expected that an effective teat dip will achieve at least a 3 and preferably about a 4 or 5 log reduction in the geometric mean of the recoverable bacteria population. Products which perform satisfactorily in this screening procedure are likely to prove effective in definitive efficacy trials based on prevention of intramammary infection.

The results obtained with the teat dip of Example 9, the positive and negative control against two different pathogens are listed in Tables 4 and 5 below.

TABLE 4

Evaluation of germicidal activity of Various Treatments on Excised Teats applied with *Staphylococcus aureus* Newbould 305).

| Treatment | Geometric Mean | Dilution Factor | Log | Log Reduction |
|---|---|---|---|---|
| Negative Control (No Sanitizer Applied) | 47.48 | 50,000 | 6.38 | — |
| Positive Control (1% Iodine Teat Sanitizer) | 0.21 | 50 | 1.02 | 5.36 |
| Teat Dip of Example 9 | 6.59 | 50 | 2.52 | 3.86 |

TABLE 5

Evaluation of Germicidal Activity of Various Treatments on Excised Teats Applied with *Streptococcus agalactiae* (Cornell 48)

| Treatment | Geometric Mean | Dilution Factor | Log | Log Reduction |
|---|---|---|---|---|
| Negative Control (No Sanitizer Applied) | 59.5 | 50,000 | 6.47 | — |
| Positive Control (1% Iodine Teat Sanitizer) | 0.71 | 50 | 1.55 | 4.92 |
| Teat, Dip of Example 8 | 3.01 | 50 | 2.17 | 4.30 |

It is apparent that the teat dip of Example 9 is effective by achieving at least a 3 log reduction in the geometric mean of the recoverable bacteria population of the pathogens employed. This effectiveness was further achieved without significant skin irritation of the excised teat.

EXAMPLE 11

The teat dip described in Example 9 was evaluated to determine the effectiveness of the teat dip in reducing the number of intramammary infections which occur during a period of experimental exposure to a high concentration of mastitis pathogens applied at milking times on an actual number of dairy cows. This challenge of actual cows with mastitis pathogens, at milking times, simulates in a qualitative way natural exposure to those organisms which are transmitted from one teat to the other or from cow to cow during the milking process. The experimental design to achieve this is set forth in Protocol B entitled "Proposed Protocol of A Teat Dip Base On Prevention Of Intramammary Infection Following Experimental Exposure Of Teats To Mastitis Pathogens", Nov. 1, 1977, published by the National Mastitis Council, 910 Seventeenth Street N.W., Washington, D.C. 20006.

The teat dip of Example 9 was evaluated with a dairy herd of 116 cows. The teats of the cows were challenged with both *Staphylococcus aureus* (Newbould 305) and *Streptococcus agalactiae* (McDonald 44).

Infection data collected during the trial are summarized below in Tables 5 and 6. The individual teats of the animals were divided into respective quarters and the bacterial status determined at initiation of the trial by collecting and culturing duplicate milk samples. Thereafter, at the afternoon milking, the lower third of all four teats of the cow was exposed to a challenge suspension containing both *Staphylococcus aureus* and *Streptococcus agalactiae* immediately after milking machines were removed. Within 5 to 10 seconds later, two teats were dipped full length with the dip and the remaining two teats served as undipped controls. Only specific quarters of the teat not initially effected with the specific pathogens were eligible for infection.

intended to be encompassed within the present invention.

What is claimed is:

1. A teat sanitizing composition comprising an aqueous dispersion of a sanitizing mixture of benzyl alcohol and phenylethanol, in an amount effective to substantially reduce the bacteria population on a teat surface when said composition is applied thereto, an emulsifying amount of a surfactant to disperse said sanitizing mixture, said composition having a pH of between about 4 and 7.

2. The composition of claim 1 wherein said composition has a pH of between about 4 to 5.

3. The composition of claim 1 wherein said composition includes an emollient.

4. The composition of claim 3 wherein said emollient is a polyhydric alcohol.

5. The composition of claim 4 wherein said polyhydric alcohol is selected from the group consisting of glycerol, sorbitol, propylene glycol, and mixtures thereof.

6. The composition of claim 1 wherein the sanitizing mixture comprises a mixture of equal amounts by weight of benzyl alcohol and phenylethanol.

7. The composition of claim 1 wherein said surfactant is selected from the group consisting of cationic, anionic, and non-ionic surfactants.

8. The composition of claim 1 wherein said surfactant

TABLE 5

Summary of efficacy data on Teat Dip of Example 9 Against *Staphylococcus aureus* (Newbould 305)

| Treatment | Teat Quarters Eligible for Infection at Beginning of Study | New Teat Quarter Infections Week | | | | | | Teat % Quarters | Reduction |
|---|---|---|---|---|---|---|---|---|---|
| | | 1 | 2 | 3 | 4 | 5 | Total | | |
| Dip of Example 9 | 211 | 2 | 0 | 2 | 0 | 2 | 6 | 2.8 | 72.0 |
| Control (No Dip Applied) | 209 | 4 | 4 | 6 | 6 | 1 | 21 | 10 | |

An examination of the above data indicates a total of 28 *S. aureus* infections were confirmed, 21 of these were in control teat quarters versus 6 in dipped teat quarters. The teat dip reduced the infection rate 72% for *S. aureus* infections and did so without chapping or irritation of teats during the study period.

is selected from the group consisting of sodium lauryl sulfate, sodium dodecyl benzene sulfonate and mixtures thereof.

9. The composition of claim 1 wherein said sanitizing mixture is present in an amount of between about 0.8 to 6% by weight of said composition.

TABLE 6

Summary of Efficacy data on Teat Dip of Example 9 against *Streptococcus agalactiae* (McDonald 44)

| Treatment | No. Teat Quarters Eligible For Infection at Beginning of Study | New Teat Quarter Infections Week | | | | | | Teat Quarters | Reduction |
|---|---|---|---|---|---|---|---|---|---|
| | | 1 | 2 | 3 | 4 | 5 | Total | | |
| Dip of Example 9 | 211 | 0 | 1 | 0 | 1 | 0 | 2 | 0.94 | 88.1 |
| Control (No Dip Applied) | 209 | 2 | 4 | 4 | 5 | 1 | 10 | 7.60 | — |

An examination of the above data indicates a total of 18 *Str. agalactiae* infections were diagnosed, 16 in control teat quarters and 2 in dipped teat quarters. The teat dip reduced the infection rate 88.1% for *Str. agalactiae* infections and did so without chapping or initiation of teats during the study period.

Although specific ingredients and results are set forth in the above Examples, these are intended to be merely illustrative of the present invention. Various other materials and/or modifications of the present invention will occur to those skilled in the art upon a reading of this disclosure. These equivalents or substitutions are 10. The composition of claim 1 wherein said sanitizing mixture is present in an amount of between about 2 to 4% by weight of said composition.

11. The composition of claim 1 wherein said surfactant is present in an amount of between about 0.5 to 6% by weight of said composition.

12. A method of sanitizing the teat of a dairy cow comprising applying thereto an aqueous dispersion of a sanitizing mixture of benzyl alcohol and phenylethanol, in an amount effective to substantially reduce the bacteria population on said teat surface once said dispersion is applied thereto, said dispersion including an emulsifying amount of a surfactant to disperse said sanitizing mixture, said dispersion containing an emollient and having a pH of between about 4 and 7.

13. The method of claim 12 wherein said composition has a pH of between about 4 to 5.

14. The method of claim 12 wherein said sanitizing mixture is present in an amount of between about 0.8 to 6% by weight of said composition.

15. The method of claim 12 wherein said sanitizing mixture is present in an amount of between about 2 to 4% by weight of said composition.

16. The method of claim 12 wherein said surfactant is present in an amount of between about 0.5 to 6% by weight of said composition.

17. The method of claim 12 wherein said surfactant is selected from the group consisting of cationic, anionic, and non-ionic surfactants.

18. The method of claim 12 wherein said surfactant is selected from the group consisting of sodium lauryl sulfate, sodium dodecyl benzene sulfonate and mixtures thereof.

19. The method of claim 12 wherein an emollient is present in said dispersion.

20. The method of claim 19 wherein said emollient is a polyhydric alcohol.

21. The method of claim 20 wherein said polyhydric alcohol is selected from the group consisting of glycerol, sorbitol, propylene glycol, and mixtures thereof.

22. The method of claim 12 wherein the sanitizing mixture comprises a mixture of equal amounts by weight of benzyl alcohol and phenylethanol.

* * * * *